United States Patent [19]

Sasamori

[11] 3,989,036
[45] Nov. 2, 1976

[54] BIOPHYSICAL ELECTRODE
[75] Inventor: Soichiro Sasamori, Higashimurayama, Japan
[73] Assignee: Dia Medical System Co., Ltd., Tokyo, Japan
[22] Filed: Apr. 2, 1975
[21] Appl. No.: 564,302

[52] U.S. Cl. .................. 128/2.06 E; 128/2.1 E; 128/417; 128/DIG. 4
[51] Int. Cl.$^2$ .................................. A61B 5/04
[58] Field of Search ........... 128/2.06 E, 2.1 E, 404, 128/410, 411, 416–418, DIG. 4

[56] References Cited
UNITED STATES PATENTS

| | | | |
|---|---|---|---|
| 2,782,786 | 2/1957 | Krasno | 128/417 |
| 2,895,479 | 7/1959 | Lloyd | 128/417 |
| 3,496,929 | 2/1970 | Dominques | 128/2.06 E |
| 3,505,993 | 4/1970 | Lewes et al. | 128/2.06 E |
| 3,508,541 | 4/1970 | Westbrook et al. | 128/2.1 E |
| 3,610,229 | 10/1971 | Zenkich | 128/2.06 E |
| 3,747,590 | 7/1973 | Motley | 128/2.06 E |
| 3,848,600 | 11/1974 | Patrick, Jr. et al. | 128/417 |
| 3,862,627 | 1/1975 | Hans, Sr. | 128/2.06 E |
| 3,882,853 | 5/1975 | Gofman et al. | 128/2.1 E |

FOREIGN PATENTS OR APPLICATIONS
216,902  7/1968  USSR ................................. 128.1 E

OTHER PUBLICATIONS
Nencmi et al, "MnO$_2$ . . . Electrodes," Med. & Biol. Eng., vol. 8, No. 2, pp. 137–143, 1970.

Primary Examiner—Robert W. Michell
Assistant Examiner—Lee S. Cohen
Attorney, Agent, or Firm—Woodhams, Blanchard and Flynn

[57] ABSTRACT

An electrode comprising a discoid, hard and porous insulating member and a conductive electrode member connected with a lead wire and closely adhering to one side of said insulating member, wherein all of these components excluding the area of the exterior of said insulating member that comes in contact with the skin are covered with a housing and said insulating member is impregnated with a solution of chloride.

8 Claims, 7 Drawing Figures

BIOPHYSICAL ELECTRODE

BACKGROUND OF THE INVENTION

The present invention relates to an electrode for the purpose of detecting electro-biophysical phenomena.

Electro-biophysical phenomena indicated by an electrocardiogram, electromyogram, electroencephalogram, etc. are clinically utilized. The biophysical potential of these phenomena is extremely low so that measurement thereof requires a technique somewhat different from that in general electronics measurement. Referring to the electrode for use in said measurement, it is required that the voltage of polarized electrode between the electrode and hypodermal tissues is low, its contact resistance is low, it can maintain a stable contact for a long time, it is free of generation of noises, to wit, change in the voltage of polarized electrode and contact resistance, and it remains in place despite physical movement of the patient.

According to the conventional electrocardiographic measurement, conductive metal plates are stuck on the spots-of-measurement by means of an electrode paste. In the conventional measurement of electroencephalogram, it is usual to paste a plate electrode on the spot-of-measurement or stick a needle electrode therein. In the case of said plate electrode, the electrode comes in contact with just the epidermis, so that the contact resistance becomes high, while in the case of said needle electrode, the electrode penetrates into the hypodermal tissues sufficiently, but the patient would be discomforted at the time of application thereof. Besides, both of these conventional electrode are defective in that the voltage of polarized electrode between the electrode and hypodermal tissues is very high. Accordingly, even a slight slipping-out of position of the electrode of physical movement of the patient would result in wide fluctuations of the voltage of polarized electrode. As the voltage of polarized electrode is fairly higher than the biophysical potential, a stable and exact measurement of biophysical potential is infeasible. As the special method of precision measurement, there is known a method employing an electrode consisting of a pressure-molded mixture of silver powder and silver chloride powder and bringing said electrode into contact with the skin through an electrode paste, which has admittedly proved fairly efficient. However, even in the case of this method, there is generated a voltage of polarized electrode considerably higher than the biophysical potential and even a slight discrepancy between the electrode and the skin would result in wide fluctuations of the voltage of polarized electrode. Accordingly, even when a silver chloride silver surface electrode is employed, an exact measurement cannot be ensured. Not only that, an electrode of this kind is very costly, so that it has not yet come into general use. Various attempts have hitherto been made with efforts centering round the problems of how to minimize the voltage of polarized electrode and how to effect correction with an amplifier in order to minimize the influence of the generated voltage of polarized electrode, but the above discussed defects still remain unremedied.

SUMMARY OF THE INVENTION

The base of the electrode according to the present invention consists of a hard and water-permeable or porous insulating member, said insulating member being impregnated with a conductive solution. By virtue of this construction, even when a voltage of polarized electrode is generated, fluctuation thereof can be extremely minimized and it is easy to effect correction by means of an amplifier or the like.

On the reverse side of a face of said insulating member impregnated with a conductive solution and that comes in contact with the skin, there is closely attached an electrode plate, said electrode plate being connected with a lead wire for transmitting the biophysical potential to the outside. Said lead wire is usually made of copper, and is connected with the electrode plate by means of solder. But, inasmuch as this solder is an alloy of tin and lead, when the copper and solder come in contact with said conductive solution, there is generated an enormous voltage of polarized electrode. Therefore, the face of the porous insulating member that comes in contact with the lead wire is provided with a film formed by applying silver powder, and the whole of said insulating member excluding the area that comes in contact with the skin is covered with a housing, whereby said housing and silver film are in airtight contact with each other and the chance of infiltration of the conductive solution is nil. Besides, application of a chloride solution as the conductive solution has the advantage of turning the silver film into silver·silver chloride which is regarded as the most stable metal. Moreover, the use of silver powder alone is economical compared with the use of silver·silver chloride from the start.

In the case of setting the electrode on a hairy spot of the skin, the electrode may fail to come in contact therewith in satisfactory condition, and therefore, the face of the electrode that comes in contact with the skin is provided with a number of projections as occasion demands.

On the occasion of a prolonged measurement, the conductive solution may dry up. Therefore, as a preventive measure, a soft, hygroscopic member is interposed between the electrode plate and the porous insulating member, or an inlet for the purpose of replenishing the conductive solution from the outside therethrough is provided. In the case of interposing a hygroscopic member, it must be firmly fixed by means of the housing so as not to bring on a change of the space between the electrode plate and the porous insulating member.

As will be clear from the foregoing description, one object of the present invention is to provide an electrode which can minimize the voltage of polarized electrode between the electrode and the hypodermal tissues and prevent fluctuation of the voltage of polarized electrode even in the case of physical movement of the patient.

Another object of the present invention is to provide an electrode which is low in contact resistance and keeps in stable contact with the skin for a long time.

A further object of the present invention is to provide an electrode which is free from drying-up of the conductive solution even during prolonged use or permits replenishment of said solution as occasion demands.

DETAILED DESCRIPTION OF THE INVENTION

Figure 1:
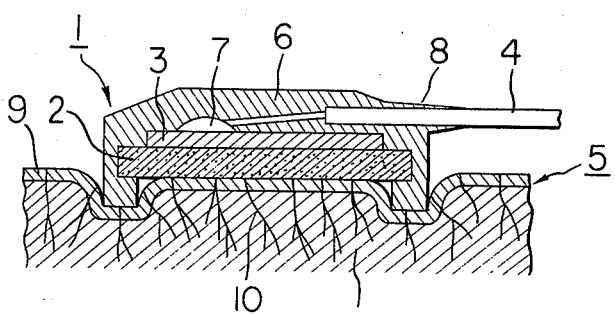
FIG. 1 is a longitudinal section of one embodiment of the electrode according to the present invention.
Figure 2:
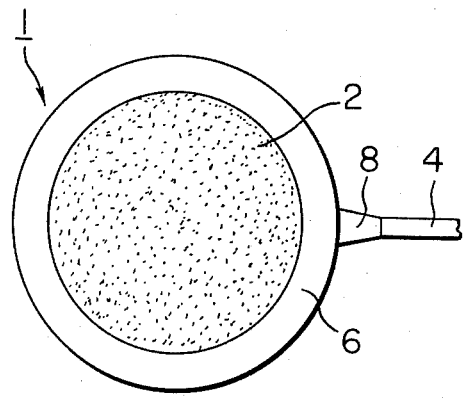
FIG. 2 is a plan view of the base of the same electrode as in FIG. 1.

In the following will be given an elucidation of particulars of the electrode according to the present invention with reference to the appended drawings.

The reference numeral 1 denotes the electrode as a whole, and this electrode 1 is composed of the porous insulating member 2, the electrode plate 3 closely attached to said porous insulating member 2, the lead wire 4 connected with said electrode plate 3, and the housing 6 covering the entire assembly excluding the area that is adapted to come in contact with the skin 5 and consisting of an insulating material. The porous insulating member 2 consists of a water-permeable, insulating material with a hardness such that it will not easily be deformed and it is formed into a disc-shape. To be precise, the material for this purpose is preferably a ceramic consisting of alumina, barium, titanate, etc., but it also will do to employ porous hard plastics, fibrous material, reticular material and the like. The discoid electrode plate 3 closely attached to one side of said porous insulating member 2 consists of a rust resistant conductive material like stainless steel, carbon, etc., and the lead wire 4 is connected with this electrode plate 3 by means of the solder 7. All of the foregoing components are covered with the housing 6 consisting of silicone resin, epoxide resin or the like, but leaving uncovered the area that is intended to come in contact with the skin 5. On the occasion of thus covering with the housing 6, for the purpose of facilitating close adherence between the housing 6 and the electrode plate 3 and also preventing occurrence of a gap between the housing 6 and the lead wire 4 which will cause infiltration of liquid inward, the extension 8 of the skirt of the housing to cover the lead wire 4 is gradually thinned and is lengthened as far as possible.

Next, on the occasion of setting this electrode on the skin 5, a conductive solution is first prepared. This conductive solution is required to be such that it will not cause eruption of the skin and it must have conductivity. As the solution for this purpose, solutions of chlorides like potassium chloride solution, sodium chloride solution and calcium chloride solution are superior and ensure stable measurement. Sodium carbonate solution is also applicable though it is somewhat defective from the viewpoint of stability of measurement. Upon preparing a solution as above, the electrode 1 is dipped therein, or the porous insulating member 2 is impregnated with said solution while removing air therefrom. Next, one side of the electrode 1 is brought into contact with the spot-of-measurement on the skin 5 in such a fashion as shown in FIG. 1 and is fixed thereon by means of an adhesive tape or the like. When the electrode is set in such a state, the solution impregnated in the porous insulating member 2 is directly connected with the hypodermal tissues 11 via the sweat-gland 10 running through the epidermis 9. This means that the hypodermal tissues 11 and the electrode plate 3 are directly interconnected by means of the solution, and therefore the contact is extremely stable. In other words, the solution functions as if it constitutes a part of the skin, and inasmuch as the porous insulating member 2 has such a hardness as will not easily get transformed, the conductive solution impregnated in said porous insulating member 2 displays no fluidity on the face of the electrode plate 3 even when the skin 5 or the electrode 1 trembles. Accordingly, protection of the electrode 1 which is the case of fluctuation of the voltage of polarized electrode can be ensured. As discussed in the foregoing, inasmuch as the electrode according to the present invention scarcely gives rise to fluctuation of the voltage of polarized electrode even when a tremble occurs between the skin 5 and the electrode 1, it brings on an excellent effect particularly in dynamic measurement such as the measurement performed on the patient while in motion, not to speak of static measurement.

Figure 3:
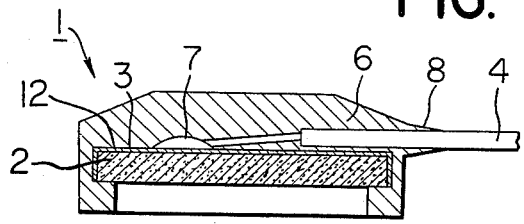
FIGS. 3 through 7 are longitudinal sections of various modifications of the electrode according to the present invention.

Next, FIG. 3 illustrates another embodiment of the present invention, wherein the exterior of the porous insulating member 2 excluding the bottom face thereof is provided a film 12 formed by baking silver powder having a mean grain size of about 20 μ. In this construction, the film 12 plays the part of the electrode plate 3 in FIG. 1, and the lead wire 4 is connected therewith by means of the solder 7. By virtue of such construction, airtight adhesion between the silver film 12 and the housing 6 is further improved, whereby infiltration of the solution toward the lead wire 4 and solder 7 can be prevented. Besides, when a chloride solution is employed as the solution, said silver film 12 will be converted into silver silver chloride and become a stable material.

Figure 4:
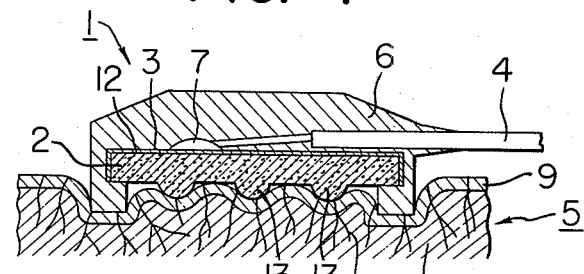

FIG. 4 illustrates still another embodiment of the present invention, wherein the bottom face of the porous insulating member 2 is provided with a number of integral projections 13. By virtue of such construction, the area that comes in contact with the skin 5 is increased, and even in the presence of hairs between the electrode and the skin, a satisfactory contact is ensured.

Figure 5:
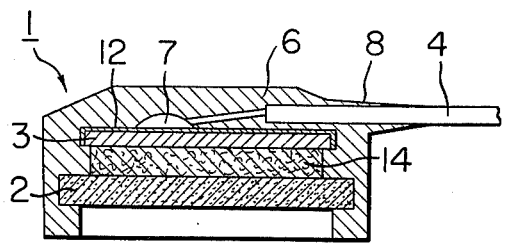

FIG. 5 illustrates yet another embodiment of the present invention, wherein a water-permeable, insulating and soft hygroscopic member 14 consisting of sponge, cotton, fiber, non-woven fabric or the like is interposed between the porous insulating member 2 and the electrode plate 3, said hygroscopic member 14 being sufficiently impregnated with the solution. Further, the electrode plate 3 is provided with the same silver film 12 as that in FIG. 3 for the purpose of improving airtight adhesion relative to the housing 6.

Figure 6:
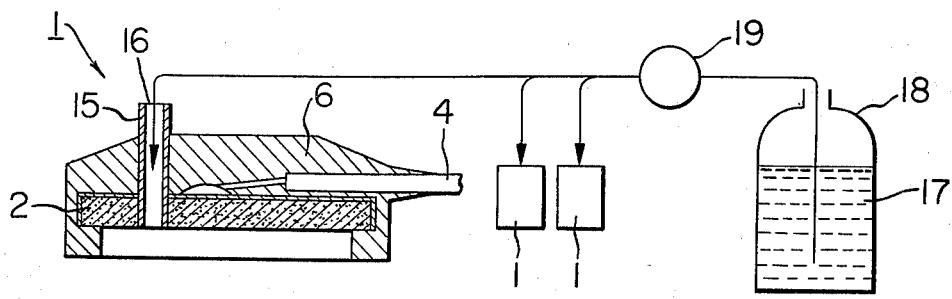

FIG. 6 illustrates an additional embodiment of the present invention, wherein the pipe 15 running from the top of the housing 6 for the electrode 1 to the bottom of the porous insulating member 2 is installed to provide the inlet 16 for the solution, whereby the solution 17 can be supplied to the electrodes 1, 1 . . . . from the container 18 storing the solution 17 by means of the pump 19. By virtue of such construction as shown in FIG. 5 or FIG. 6, drying-up of the solution on the occasion of prolonged measurement can be prevented.

Figure 7:
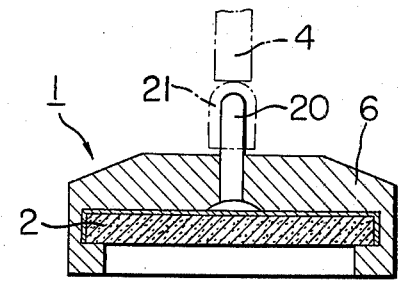

The foregoing embodiments in FIGS. 1 through 6 illustrate the case wherein the lead wire 4 is integrated with the housing 6. Meanwhile, FIG. 7 is illustrative of a particular embodiment wherein the lead terminal 20 projects to the outside of the housing 6, and the connector 21 is connected with the thus projected portion of the lead terminal 20, whereby electro-biophysical phenomena are transmitted to the outside.

What is claimed is:
1. A biophysical electrode, comprising:
 a porous, water-permeable, ceramic, insulating member of disclike shape adapted to be impregnated with a conductive liquid, said member having a portion of one surface thereof adapted to be placed in surface-to-surface contact with body tissue;

a silver coating film deposited directly on and covering the entire surface of said member except said surface portion thereof, said silver film defining an electrode;

an insulating housing encapsulating and in air-tight contact with said silver film, said housing having an opening exposing said surface portion of said member; and an electrical conductive lead in electrical contact with said silver film and extending through the housing.

2. A biophysical electrode as claimed in claim 1 in which said ceramic insulating member is made of alumina.

3. A biophysical electrode as claimed in claim 2 in which said ceramic insulating member is impregnated with a solution of a chloride selected from the group consisting of potassium chloride, sodium chloride and calcium chloride.

4. A biophysical electrode as claimed in claim 1 in which said exposed surface portion of said ceramic insulating member has a plurality of integral projections extending outwardly therefrom.

5. A biophysical electrode as claimed in claim 1 including a conduit connected to said ceramic insulating member and extending through said silver film and said housing and adapted for supplying the conductive liquid to said ceramic insulating member.

6. A biophysical electrode as claimed in claim 1 wherein said lead is a terminal that projects through the housing and terminates adjacent to the outside thereof and is adapted for electrical connection to a conductor.

7. A biophysical electrode as claimed in claim 1 wherein said lead is an electrical wire.

8. A biophysical electrode as claimed in claim 1 in which said ceramic insulating member is a planar disc, said silver film covers the edge and one surface of said disc, the other surface of said disc forming said surface portion, and said housing has a marginal edge portion of the opening thereof overlapping the marginal edge portion of the other surface of said disc.

* * * * *